(12) United States Patent
Czipott et al.

(10) Patent No.: US 7,315,166 B2
(45) Date of Patent: Jan. 1, 2008

(54) MAGNETIC RESONANCE IMAGING SCREENING METHOD AND APPARATUS

(75) Inventors: Peter V. Czipott, San Diego, CA (US); Sankaran Kumar, San Marcos, CA (US); Stephen Wolff, San Diego, CA (US); Lowell J. Burnett, El Cajon, CA (US); Richard J. McClure, San Diego, CA (US); R. Kemp Massengill, Leucadia, CA (US); William F. Avrin, San Diego, CA (US)

(73) Assignees: MedNovus, Inc., Leucadia, CA (US); Quantum Magnetics, Inc., San Diego, CA (US)

( * ) Notice: Subject to any disclaimer, the term of this patent is extended or adjusted under 35 U.S.C. 154(b) by 744 days.

(21) Appl. No.: 10/681,033

(22) Filed: Oct. 7, 2003

(65) Prior Publication Data
US 2004/0147833 A1    Jul. 29, 2004

Related U.S. Application Data

(60) Provisional application No. 60/440,697, filed on Jan. 17, 2003, provisional application No. 60/489,250, filed on Jul. 22, 2003.

(51) Int. Cl.
    *G01R 33/00* (2006.01)
(52) U.S. Cl. ............... 324/244; 324/228; 324/260
(58) Field of Classification Search ............ 600/407, 600/409–419, 420–421; 324/228, 232, 234, 324/239, 242–244, 260, 173–174
See application file for complete search history.

(56) References Cited

U.S. PATENT DOCUMENTS

| 3,781,664 A | 12/1973 | Rorden |
| 3,971,983 A | 7/1976 | Jaquet |
| 4,060,039 A | 11/1977 | Lagarrigue |
| 4,068,164 A | 1/1978 | Schwartz et al. |
| 4,135,183 A | 1/1979 | Heltemes |
| 4,193,024 A | 3/1980 | Hoult et al. |
| 4,734,643 A | 3/1988 | Bubenik et al. |
| 4,837,489 A | 6/1989 | McFee |
| 5,175,419 A | 12/1992 | Yamashita |

(Continued)

FOREIGN PATENT DOCUMENTS

WO    WO 03/091753 A1    11/2003

(Continued)

OTHER PUBLICATIONS

ETS-Lindgren; *Ferroguard Unveiled at RSNA 2003*; The Quiet Zone; Jan. 2004; p. 11.

(Continued)

*Primary Examiner*—Bot LeDynh
(74) *Attorney, Agent, or Firm*—Gerald W. Spinks

(57) ABSTRACT

A method and apparatus to screen individuals specifically for paramagnetic or ferromagnetic objects they may be carrying or wearing, before they enter the high-field region of an MRI suite. The device comprises either a screening portal or a compact, hand-held magnetic gradiometer and its electronics. The device places all of the sensor arrays in close proximity to all parts of a subject's body, for screening purposes.

43 Claims, 5 Drawing Sheets

U.S. PATENT DOCUMENTS

| | | | |
|---|---|---|---|
| 5,321,361 | A | 6/1994 | Goodman |
| 5,379,334 | A | 1/1995 | Zimmer et al. |
| 5,397,986 | A | 3/1995 | Conway et al. |
| 5,408,178 | A | 4/1995 | Wikswo, Jr. et al. |
| 5,493,517 | A | 2/1996 | Frazier |
| 5,494,033 | A | 2/1996 | Buchanan et al. |
| 5,494,035 | A | 2/1996 | Leuthold et al. |
| 5,504,428 | A | 4/1996 | Johnson |
| 5,610,518 | A | 3/1997 | Chamberlain, IV |
| 5,689,184 | A | 11/1997 | Jeffers et al. |
| 5,705,924 | A | 1/1998 | Jeffers |
| 5,735,278 | A | 4/1998 | Hoult et al. |
| 5,757,183 | A | 5/1998 | Smith et al. |
| 5,842,986 | A | 12/1998 | Avrin |
| 6,064,208 | A | 5/2000 | Steckner |
| 6,087,832 | A | 7/2000 | Doty |
| 6,133,829 | A | 10/2000 | Johnstone et al. |
| 6,150,810 | A | 11/2000 | Roybal |
| 6,208,884 | B1 | 3/2001 | Kumar et al. |
| 6,362,739 | B1 | 3/2002 | Burton |
| 6,384,603 | B2 | 5/2002 | Hoult et al. |
| 6,418,335 | B2 | 7/2002 | Avrin et al. |
| 6,496,713 | B2 | 12/2002 | Avrin et al. |
| 6,541,966 | B1 | 4/2003 | Keene |
| 6,670,809 | B1 | 12/2003 | Edelstein et al. |
| 2002/0115925 | A1 | 8/2002 | Avrin et al. |
| 2002/0151779 | A1 | 10/2002 | Avrin et al. |
| 2003/0083588 | A1 | 5/2003 | McClure et al. |
| 2003/0171669 | A1 | 9/2003 | Kopp |
| 2003/0216632 | A1 | 11/2003 | McClure et al. |
| 2004/0135687 | A1 | 7/2004 | Keene |

FOREIGN PATENT DOCUMENTS

| | | |
|---|---|---|
| WO | WO 03091753 | 11/2003 |
| WO | WO 2004/044620 A1 | 5/2004 |

OTHER PUBLICATIONS

ETS-Lindgren Website; *Ferromagnetic Detection System*; May 29, 2004; 2 pages.

CMP United Business Media Website; Metal detector guards the door to screen ferromagnetic objects; Diagnostic Imaging SCAN; Jan. 28, 2004; 2 pages.

Finn, Edward J., et al., Ferromagnetic Materials in Patients: Detection before MR Imaging; Radiology; Jul. 1985; vol. 185; pp. 139-141.

Institute For Biodiagnostics; MRI Safety: Detection of Ferromagnetic Objects; Date unknown; 8 pages; National Research Council Canada.

Kopp Development; Ferralert Brochure; Date Unknown; 2 pages; Kopp Development; Jensen Beach, FL.

Kotter, David K., et al. . ; Abstract: Detection and Classification of Concealed Weapons Using a Magnetometer-based Portal; NASA ADS Instrumentation Abstract Service; Aug. 2002; 1 page; The International Society for Optical Engineering.

Melodi Metal Locator Gets Straight to the Point; Medica 2002; Nov. 2002; 4 pages; Düsseldorf, Germany.

Metal Detector Finds Lost Coins in Kids; CNN.com/Technology; Jan. 29, 2003; 2 pages; Cable News Network.

Quantum Magnetics; i-Portal 100 Advanced Weapons Detection Portal Brochures; Date unknown; 8 pages.

Mednovus/Quantum Magnetics; SAFESCAN Portal 9000 Series Brochure; 1 page.

Finn, Edward J., et al., Ferromagnetic Materials in Patients: Detection before MR Imaging; Radiology; Jul. 1985; vol. 185; pp. 139-141.

Institute For Biodiagnostics; MRI Safety: Detection of Ferromagnetic Objects; Date unknown; 8 pages; National Research Council Canada.

Kopp Development; Ferralert Brochure; Date Unknown; 2 pages; Kopp Development; Jensen Beach, FL.

Kotter, David K., et al. . ; Abstract: Detection and Classification of Concealed Weapons Using a Magnetometer-based Portal; NASA ADS Instrumentation Abstract Service; Aug. 2002; 1 page; The International Society for Optical Engineering.

Melodi Metal Locator Gets Straight to the Point; Medica 2002; Nov. 2002; 4 pages; Düsseldorf, Germany.

Metal Detector Finds Lost Coins in Kids; CNN.com/Technology; Jan. 29, 2003; 2 pages; Cable News Network.

Quantum Magnetics; i-Portal 100 Advanced Weapons Detection Portal Brochures; Date unknown; 8 pages.

Mednovus/Quantum Magnetics; SAFESCAN Portal 9000 Series Brochure; 1 page, Date unknown.

MAGNETIC RESONANCE IMAGING SCREENING METHOD AND APPARATUS

CROSS REFERENCE TO RELATED APPLICATIONS

This application relies upon U.S. Provisional Pat. App. No. 60/440,697, filed Jan. 17, 2003, for "Method and Apparatus to Use Magnetic Entryway Detectors for Pre-MRI Screening", and U.S. Provisional Pat. App. No. 60/489,250, filed Jul. 22, 2003, for "Ferromagnetic Wand Method and Apparatus for Magnetic Resonance Imaging Screening".

STATEMENT REGARDING FEDERALLY SPONSORED RESEARCH OR DEVELOPMENT

Not Applicable

BACKGROUND OF THE INVENTION

1. Field of the Invention

The present invention is in the field of methods and apparatus used to prevent the presence of paramagnetic or ferromagnetic objects near a magnetic resonance imaging (MRI) system.

2. Background Art

Paramagnetic and ferromagnetic objects are highly unsafe near MRI systems, because the strong magnetic gradients caused by MRI magnets exert a strong force on such objects, potentially turning them into dangerous missiles. Several accidents, some fatal, are known to have occurred as the result of someone inadvertently carrying such an object into the MRI room. Current MRI safety practices rely on signage and training to prevent people from taking such objects into the MRI chamber. There is currently no known technical means in use to prevent the accidental transportation of such objects into the MRI chamber, or even to warn of such an occurrence.

Use of conventional metal detectors, whether portals or wands, would not be efficient for this purpose, because they do not distinguish between magnetic and non-magnetic objects, and only magnetic objects are dangerous. Conventional systems generate an audio-band oscillating or pulsed magnetic field with which they illuminate the subject. The time-varying field induces electrical eddy currents in metallic objects. It is these eddy currents which are detected by the system, to reveal the presence of the metallic objects. There is no discrimination between ferromagnetic objects, which are dangerous near an MRI system, and non-magnetic objects, which are not. As a result, conventional systems would generate far too many false alarms to be usable in this application. The invention described herein solves the problem by detecting only paramagnetic and ferromagnetic objects, which are exactly those that must be excluded from the MRI room.

BRIEF SUMMARY OF THE INVENTION

The present invention provides an apparatus and a method for scanning a patient or attendant for the presence of an object which is either permanently magnetic or susceptible to being magnetized by an external field. The sensors in this scanning apparatus can be mounted on either a wand type frame, or a portal type frame. Either embodiment positions the entire sensor array in proximity to every portion of a patient or other individual. The wand embodiment of the scanner can be passed in proximity to every portion of the subject's body. The portal embodiment of the scanner arranges the sensors in a horizontal alignment, making the sensor array suitable for positioning every sensor in proximity to the body of a recumbent patient, as the patient passes through the portal.

The sensors can detect the magnetic field of the object, whether the object is a permanent magnet or merely susceptible to magnetization. Where an external field induces a magnetic field in the object, the external field may be the Earth's magnetic field, or it may be generated by another source, such as a nearby MRI apparatus or a dedicated source such as one mounted on the frame of the apparatus.

The novel features of this invention, as well as the invention itself, will be best understood from the attached drawings, taken along with the following description, in which similar reference characters refer to similar parts, and in which:

DETAILED DESCRIPTION OF THE INVENTION

Figure 1:
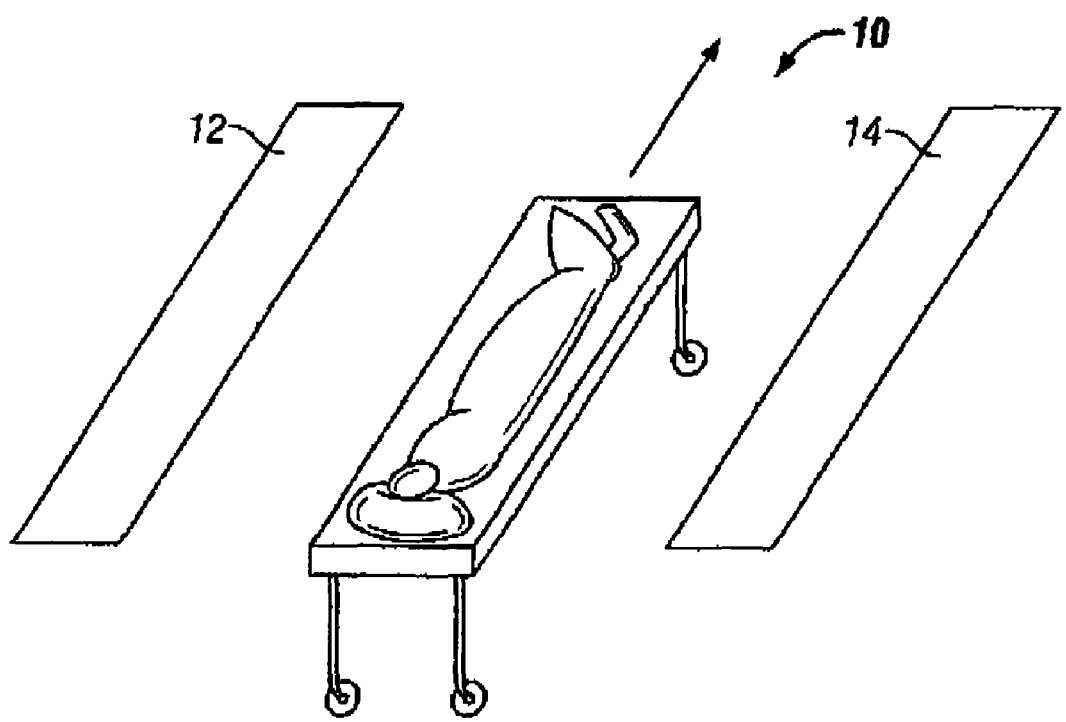
FIG. 1 is a schematic showing the horizontal arrangement of sensor arrays in a first portal type embodiment.

The present invention, which applies to both permanently magnetic objects called "hard" ferromagnets and non-permanent magnetically susceptible objects called "soft" ferromagnets, can use magnetometers with good sensitivity at frequencies all the way, or nearly, to DC, i.e., zero frequency. This allows several modes of use:

(1) As a completely passive system, the present invention detects ferromagnetic objects using their permanent magnetization, in the case of "hard" ferromagnets, or the magnetization induced by the Earth's magnetic field, in the case of "soft" ferromagnets.

(2) As a DC magnetic susceptometer, the present invention applies a static DC magnetic field, allowing control and usually enhancement of the magnetization of soft ferromagnets, thus enhancing their detectability.

(3) As an AC magnetic susceptometer, the present invention applies an oscillating AC magnetic field, but at very low frequencies compared to conventional detectors, allowing enhancement of their magnetization. The purpose of AC illumination is to move the signal from DC to a region of lower noise at finite frequency. The AC frequency is chosen to avoid inducing the electrical eddy currents detected by other systems, to suppress the response from non-ferromagnetic metal objects, and thus maintaining the discrimination capability.

The present invention importantly arranges an array of sensors in such a way that the entire sensor array can be placed in proximity to all portions of the body of a subject, such as a patient or an attendant. In particular, the sensor arrays are arranged so as to be susceptible to placement in proximity to all portions of the body of a patient lying recumbent, as on a stretcher or gurney. This object is accomplished by either of two major embodiments of the invention: a portal structure, and a hand held wand. The portal structure is designed to have one or more horizontally arranged sensor arrays, suitable for alignment of the entire sensor array with a recumbent patient. This differs from a portal arrangement in which the sensor arrays are arranged vertically, placing only a few of the sensors in proximity to a recumbent patient. The wand is susceptible to movement over the body of the subject in order to place the entire sensor array in proximity to all portions of the subject's body.

A passive magnetic embodiment of the portal used in one embodiment of the present invention can be similar in some respects to the SecureScan 2000™ weapons detection portal which is manufactured by Quantum Magnetics, Inc., and marketed by Milestone Technology, Inc., or the i-Portal™ weapons detection portal which is marketed by Quantum Magnetics, Inc. In important respects, however, the portal would be modified to be suitable for use in the present invention, namely, to make it suitable for use with a recumbent subject lying on a gurney or stretcher, rather than walking upright. In the known configuration, patients on gurneys would be too distant from too many of the sensors for adequate detection.

The portal includes two panels of sensors on the sides of the entryway. An array of magnetometers inside each panel enables detection, characterization, and localization of ferromagnetic objects from the soles of the feet to the top of the head. The magnetometer array can take a variety of configurations, and it can use a variety of sensor technologies. For example, a set of 16 single-axis magnetic gradiometers can be arranged with 8 in each panel. Other configurations can include arrays of multi-axis gradiometers, or combinations of single-axis and multi-axis gradiometers. One or more magnetic tensor gradiometers may also be used. A magnetoresistive magnetometer, or any other sensor capable of sensing magnetic field changes at or near zero frequency, can be used.

As shown in FIG. 1, in order to scan a patient on a gurney, the portal sensor configuration 10 of the present invention must be arranged to bring all of the sensors closer to the patient and to effectively scan a patient in the recumbent position. Rather than being arranged vertically as in the aforementioned known portals, the two sensor panels 12, 14 can be arranged horizontally, parallel to the path of the gurney and on either side, as shown in FIG. 1. This places the sensors in a similar relation to the patient as they would have, in the vertical arrangement, to an ambulatory patient. Also, a single "snapshot" of data covers the entire gurney and patient, as in the ambulatory case. The sensor panels 12, 14 can be permanently arranged horizontally, or they can pivot to this configuration.

Figure 2:
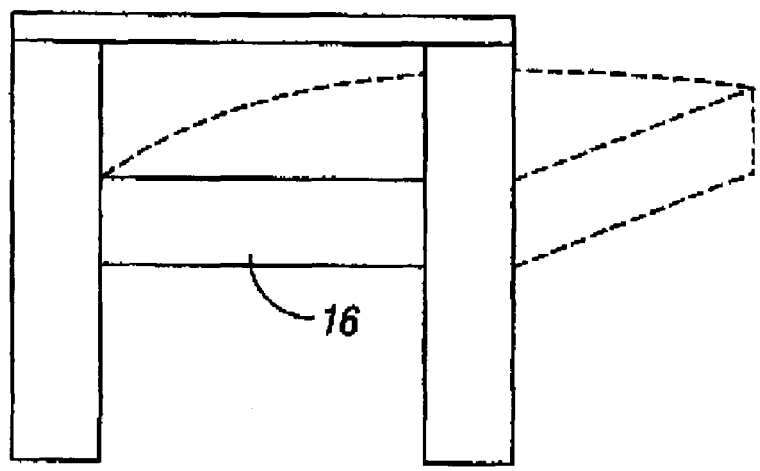
FIG. 2 is a schematic of a second portal embodiment.
Figure 3:
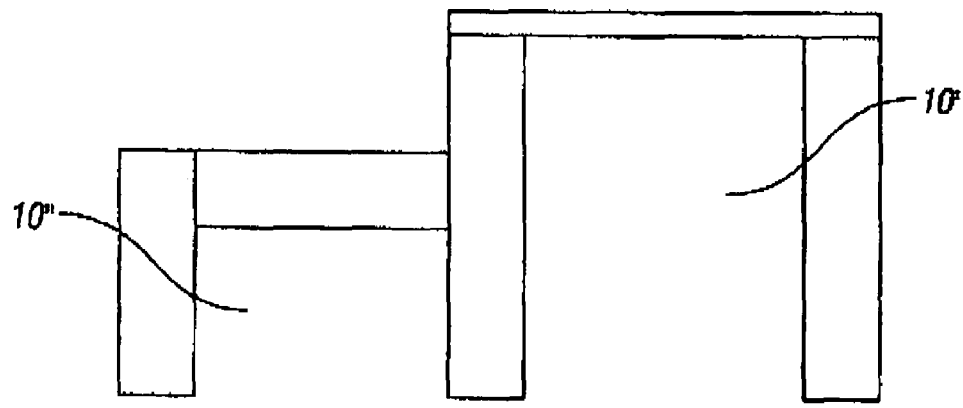
FIG. 3 is a schematic of a third portal embodiment.

Alternatively, in addition to the vertically arranged sensor panels as in the aforementioned known portals, the portal can have a "dutch door" with an additional, horizontal, sensor panel 16 in the upper half of the door, just high enough to clear a patient on a gurney, as shown in FIG. 2. As the patient is wheeled under the upper door, the patient would pass in close proximity to the horizontal sensor panel 16, allowing all of its sensors to scan the patient from head to foot, or vice versa. This gives the best detection and resolution of objects, since more sensors are placed closer to the patient. Then, the attendant would push the dutch door open and walk through the portal, being scanned by the vertically arranged sensor panels. The "dutch door" array 16 can be spring loaded, so that it moves out of the way for an ambulatory subject. A microswitch indicator can tell the software whether the door is engaged, for a recumbent patient, or disengaged, for an ambulatory subject. As a variation of this embodiment, a portal with vertically arranged sensor panels can be situated next to a portal with a horizontally arranged sensor panel, as shown in FIG. 3.

As an alternative to the passive magnetic portal, an AC or DC magnetizing field can be provided by one or more source coils, a DC field can be provided by a permanent magnet array, or a DC field can be provided in the form of the fringing field of a nearby MRI magnet. In any case, a computer is provided to interrogate the sensors and to interpret the magnetic signals, to detect, characterize, and locate ferromagnetic objects. Characterization of the object provides the size and orientation of its magnetic moment, which can be related to the physical size of the object, and to the magnitude of the attractive magnetic force. The analysis software can use various known algorithms, or a neural network can be used. The information gained can be related to a photographic image of the subject, for the purpose of locating the ferromagnetic object on the subject. A light display can be used to indicate the approximate location of the detected object. System diagnosis, monitoring, and signal interpretation can be done via the Internet, if desired.

As an alternative to the portal type screening apparatus, a hand-held device can be used to screen individuals specifically for strongly paramagnetic or ferromagnetic objects they may be carrying or wearing, before they enter the high-field region of an MRI suite. In some instances, the lack of floor space precludes a fixed installation such as the portal disclosed above. In these cases, a hand wand may be the preferred embodiment.

The hand-held device, or wand, comprises a compact magnetic gradiometer and its electronics. The gradiometer can measure either a single gradient component, multiple components, or the complete gradient tensor. The gradiometer comprises one or more pairs of magnetic sensors and reads out the difference signal between members of each pair. Background fields have small gradients, so the difference signal resulting from these is small. Close to a paramagnetic or ferromagnetic body, however, field gradients are strong; they vary as $1/r^4$ with the distance r from the sensor to the magnetic body. A strong anomaly is sensed whenever the wand is passed close by such an object of interest. The wand does not detect nonmagnetic metals. Its electronics read the signals out and process them. The output can be in the form of a simple alarm when the signal exceeds a threshold. More robust processing algorithms can incorporate adaptive background cancellation to further suppress background gradient interference, and target-object localization in the case of full tensor gradiometer implementations.

To increase the signal from the target object, it can be desirable to make the measurement in a stronger ambient field than the earth's magnetic field, which is about 0.5 Gauss. The fringing field from a magnetic resonance imaging (MRI) magnet can provide such an enhanced field, with strengths in excess of 10 Gauss.

A further embodiment combines the magnetic wand with a wire coil that can be used, by means of driving electric current through it, to generate a controlled source field. The coil can be configured to suppress its common-mode signal on the gradiometer sensors but provide a magnetizing field around the wand. This field, by magnetizing paramagnetic or ferromagnetic objects, increases their signal relative to the background. The field can be static (DC) or time-varying (AC). The benefit of an AC field is that the system can work at a non-zero frequency, further suppressing background interference. The frequency is chosen to be low enough, however, not to excite a response from conductive but nonmagnetic objects.

This device consists of a rigid, non-metallic, non-magnetic structure that supports one or more pairs of magnetometers. Each pair consists of sensors aligned to measure the same component of the magnetic field. Each pair's two outputs are differenced to create the gradient signal. Sensor electronics operate the sensors and perform the differencing. They also operate signal processing algorithms to suppress background interference and to alarm in the proximity of paramagnetic or ferromagnetic objects.

In embodiments involving an active magnetic source, the wand also has one or more coils of wire and electronics to drive controlled currents in the coils, to act as a magnetizing source field. The coils are designed to produce a zero differential signal on the gradiometers, in the absence of nearby magnetic objects.

In a further embodiment, an applied DC magnetic field can be created by means of one or more permanent magnets mounted in the wand. The magnets are mounted such that their primary magnetic field is oriented orthogonally to the sensitive axis of the magnetometers in the wand. In this way, the sensors are not saturated by the applied DC field, but remain sensitive to enhanced magnetization of a ferromagnetic object by that field. Use of permanent magnets to generate the field has an advantage over using a coil, namely, the permanent magnet draws no power. However, a potential disadvantage is that the magnetic field cannot be turned off, so the wand must be stored carefully when not in use.

The use of AC fields enables the use of induction coil sensors, in addition to or instead of magnetometers, like magnetoresistive, fluxgate, and other types. Induction coil sensors are impossible to use in the DC embodiment because the induction coil has zero sensitivity at zero frequency. Using induction coil sensors typically reduces the cost of the product without sacrificing sensitivity in the AC system. Using induction coil sensors confers a particular advantage, in that it renders the wand insensitive to interference from noise induced by the wand's motion in the Earth's field. This is a major potential source of interference in the case of the DC applied field.

An AC system could make use of two different excitation directions—operating at two different frequencies, to avoid crosstalk—which can improve detection of long, narrow objects, which are precisely the shape that is most dangerous in this situation.

The wand can be extended into a two-dimensional array of sensors to enable reliable scanning without as much moving of the wand back and forth. Too large an array becomes unwieldy and expensive; the optimum array size depends upon the balance between cost, reliability, and user skill found in any given application.

Figure 4:
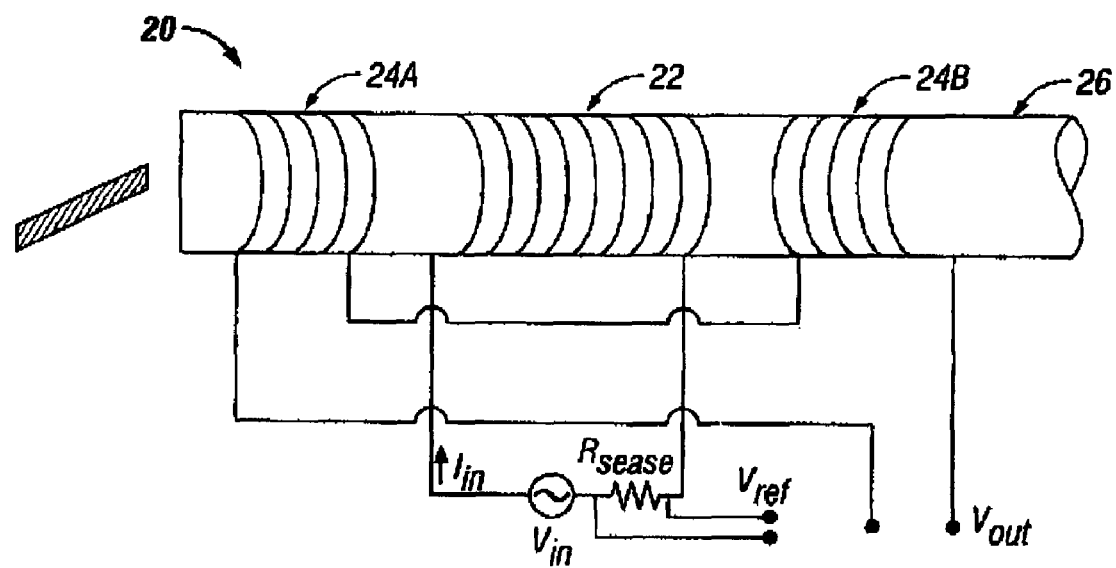
FIG. 4 is a schematic of a first wand embodiment.
Figure 5:
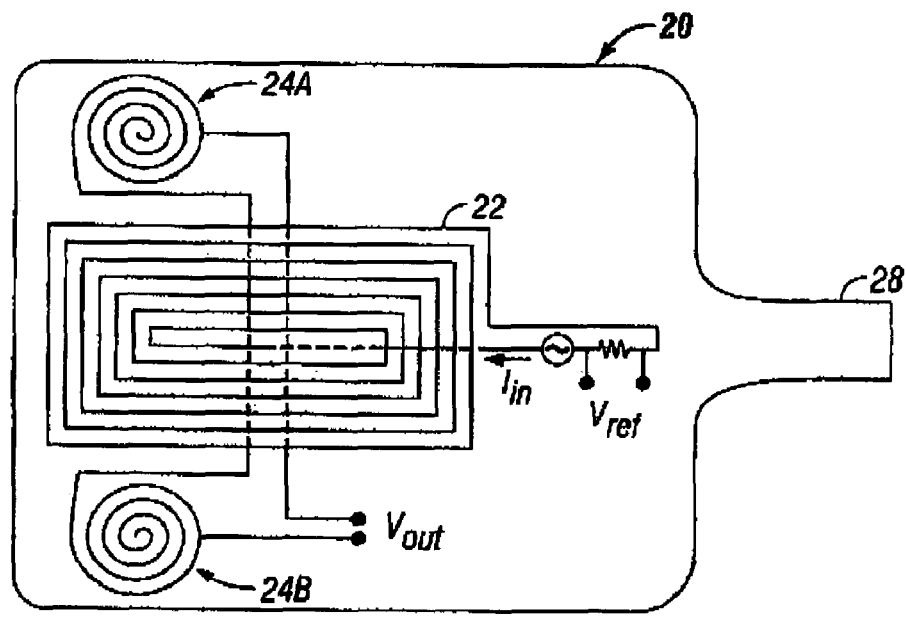
FIG. 5 is a schematic of a second wand embodiment.

FIGS. 4 and 5 illustrate the principles of the wand embodiments 20 of the invention, utilizing an AC source. An excitation coil 22, by means of a sinusoidal (AC) current driven in it, generates an alternating magnetic field that excites a combination of magnetization current and electrical eddy current in any conductive and/or ferromagnetic and/or magnetically permeable body nearby. The excitation frequency is chosen to be low enough so that the magnetization (or, equivalently, magnetic susceptibility) response of objects to be detected exceeds their eddy current response. The choice of frequency remains to be determined, but it is expected to be several tens of hertz (Hz), or at least substantially less than 1 kHz.

The excitation current can be driven by any number of standard drive circuits, including either direct drive (controlled voltage source in series with the coil) or a resonant drive (voltage source coupled to the coil via a series capacitance whose value is chosen such that, in combination with the coil's self-inductance, the current is a maximum at a desired resonant frequency given by $1/2\pi(LC)^{1/2}$).

In both FIGS. 4 and 5, the receiver or sensor coil is, in fact, made of two coils 24A and 24B, wound in opposite senses and connected in series. They form what is well-known as a gradiometer; a uniform magnetic flux threading both coils produces zero response. Coils 24A and 24B are distributed symmetrically about the excitation coil 22 such that, in the absence of any target object (which is conductive, magnetic or magnetically permeable) nearby, each senses an identical flux from the excitation which thus cancels out. A handle 28 can contain the electronics and a battery.

Although the intent is to make the two coils 24A and 24B perfectly identical, and to place them in identically symmetric locations, in practice one falls short of the ideal. As a result, any actual embodiment will display a nonzero response to the excitation, even in the absence of a target; this residual common-mode signal is referred to as an "imbalance" signal. Standard electrical circuits can zero out the imbalance signal by adding an appropriately scaled fraction of the reference voltage $V_{ref}$ (a voltage proportional to the excitation current, obtained by measuring across a series monitor resistor) to the output voltage $V_{out}$.

When a target object is near to either coil 24A or 24B, it spoils the symmetry and thus induces a finite signal. This signal oscillates at the same frequency as the excitation. Standard demodulation or phase-sensitive detection circuits, using $V_{ref}$ as the phase reference, measure the magnitude of $V_{out}$ in phase with $V_{ref}$ and in quadrature (90 degrees out of phase) with $V_{ref}$. At an appropriately chosen low frequency, the response will be dominated by the susceptibility response, which appears predominantly in the quadrature output, as opposed to the eddy current response, which appears predominantly in the in-phase component.

In principle, the coils 24A and 24B could be replaced by two magnetometer sensors (fluxgate, magnetoresistive, magnetoimpedance, etc.). Coils respond to the time derivative of the magnetic field, while magnetometers respond to the field itself; the coil's output voltage is shifted by 90 degrees with respect to a magnetometer's. If magnetometers are used instead of coils, then the susceptibility response would show up in the in-phase component and the eddy current response (at low frequency) in the quadrature component.

If the operating frequency is chosen much too high, both susceptibility and eddy-current responses appear in the in-phase component (using magnetometers) or quadrature component (using coils), but with opposite sign, making it impossible to distinguish between the two. At intermediate frequencies, the eddy current phase is intermediate between the two components, complicating the distinction. Therefore, it is important to choose the excitation frequency to be low enough, and preferably less than about 1000 Hz.

The substrate or coil form 26 must be nonconductive, nonferromagnetic and, with one possible exception, magnetically impermeable ($\mu=\mu_o$, where $\mu_o$ is the permeability of free space). The exception is that a magnetically permeable core inside the sense coils 24A, 24B (practical only in the cylindrical geometry of FIG. 4) can increase the sensitivity of the system.

Using a resonant drive circuit for the excitation coil 22 may significantly reduce the electrical power needed to create the excitation. Thus, this embodiment may be preferred for a battery-operated, hand-held wand. The other circuits, including demodulation, threshold, discrimination, and alarm/alert, require negligible power, so the system power is dominated by the excitation requirement.

Figure 6:
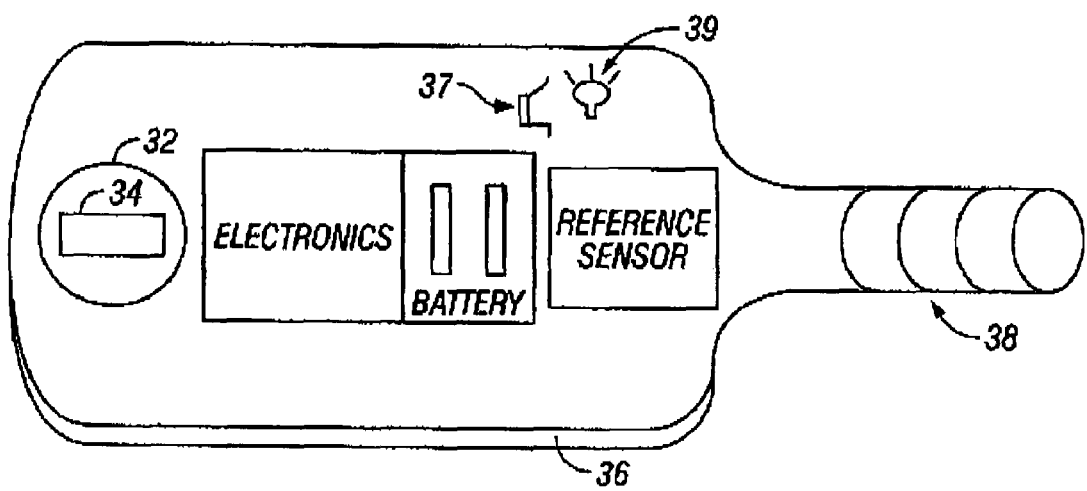
FIG. 6 is a schematic of a third wand embodiment.

As shown in FIG. 6, the DC embodiment of the wand 30 can have a sensor board with 2 sensors 34, which can be placed at each end of an epoxy fiberglass paddle 36. A DC magnetic field source 32, such as a permanent magnet, an example of which is a ferrite disc, can be mounted in such a manner as to provide a normal (perpendicular) magnetic field at the sensor 34. The concept of this arrangement is to provide an external magnetic field source to induce magnetization in any local ferromagnetic body, so that the sensor 34 can detect that body, while, at the same time providing no in-the-plane-of-the-sensor active-axis magnetic field.

The use of a reference sensor helps to eliminate common mode error signals. For instance, a nearby passenger conveyer, such as a gurney, could contain magnetic components, but this spurious magnetization is not what is intended to detect, and, therefore, it is preferable to eliminate this magnetic source. An audio alert 37, such as a buzzer, and/or an alarm light 39 can be employed to signal the presence of an unwanted ferromagnetic object. A ferromagnetic bobby pin is an example of such an unwanted ferromagnetic object.

A non-ferromagnetic covering material, constructed, for instance, of a substance such as aluminum or nylon, or other suitable material, can surround the wand 30. This type of covering is not only protective; it also facilitates removal of any ferromagnetic objects which might stick to the wand.

Figure 7:
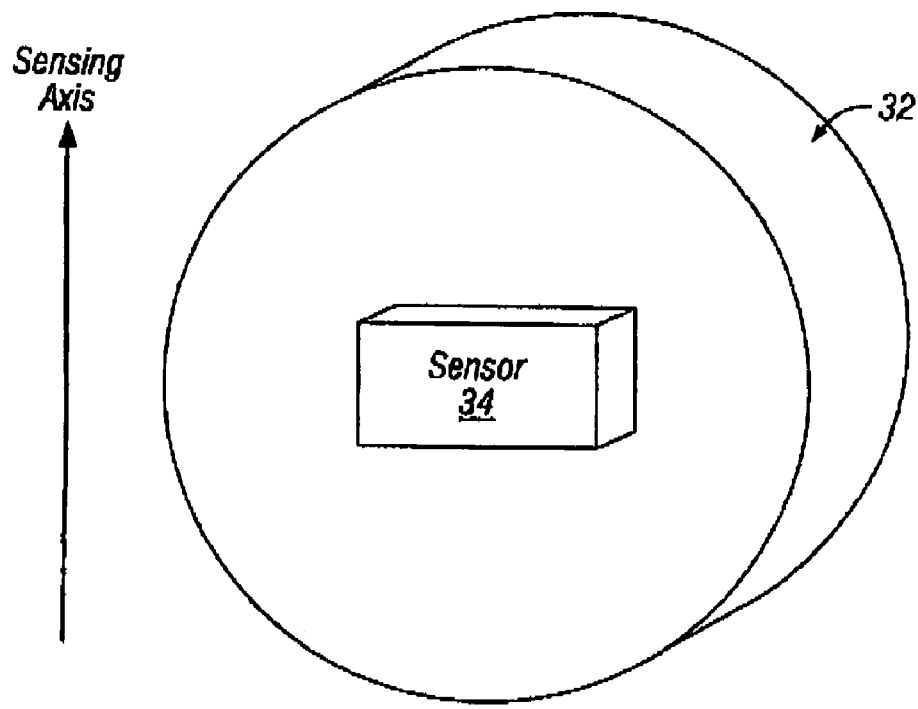
FIGS. 7 through 10 are schematics of several embodiments of the arrangement of the source fields and sensors.

As shown in FIG. 7, the sensor's sensitivity axis is orthogonal to the axis of the magnetic field of the permanent magnet 32. Otherwise stated, the magnetic field of the permanent magnet 32 is normal to the plane of the sensor 34.

Figure 8:
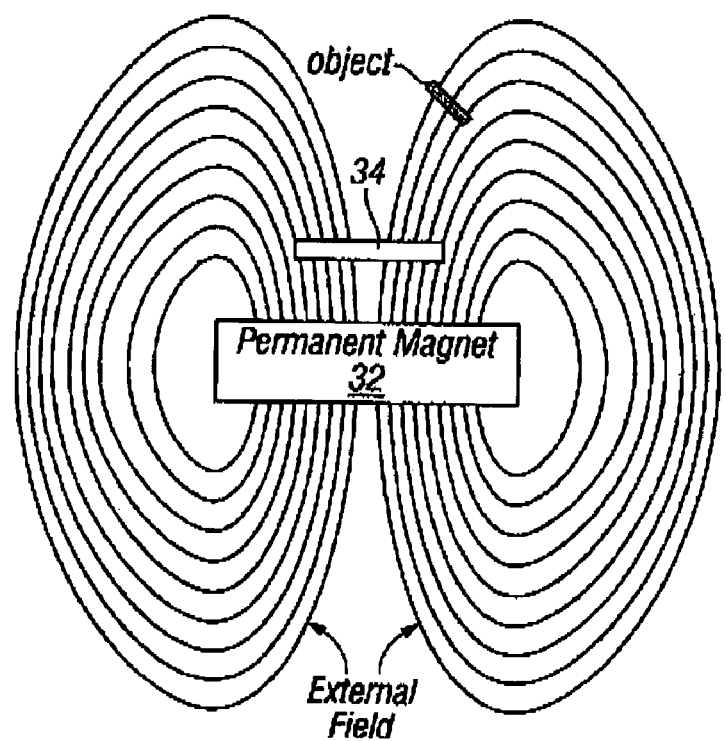
Figure 9:
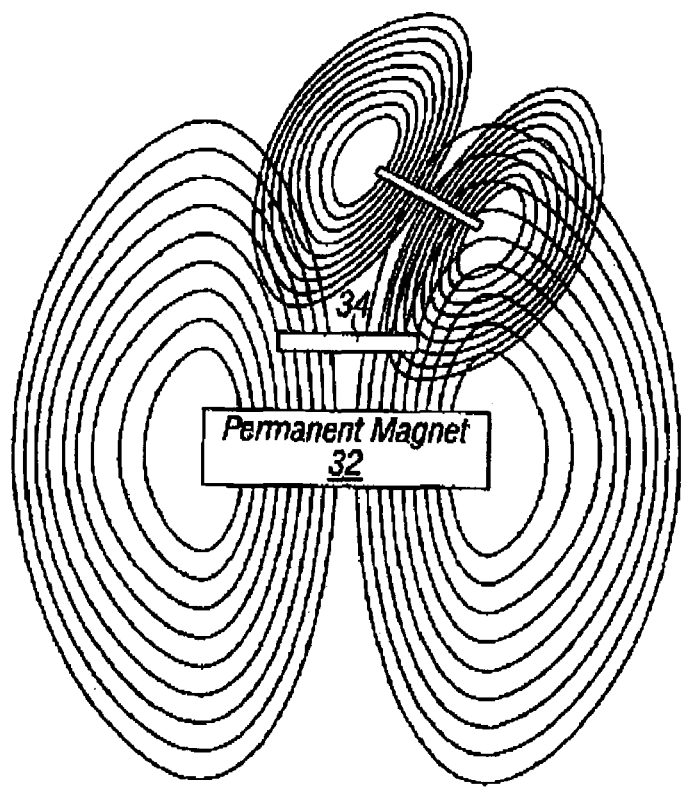

In FIG. 8, the magnetic field of the DC permanent magnet field source 32 magnetizes the ferromagnetic object, which then has a magnetic field of its own, as shown in FIG. 9. This induced magnetization ("demag field") is detected by the sensor 34, triggering the alarm buzzer 37 and/or light 39.

Figure 10:
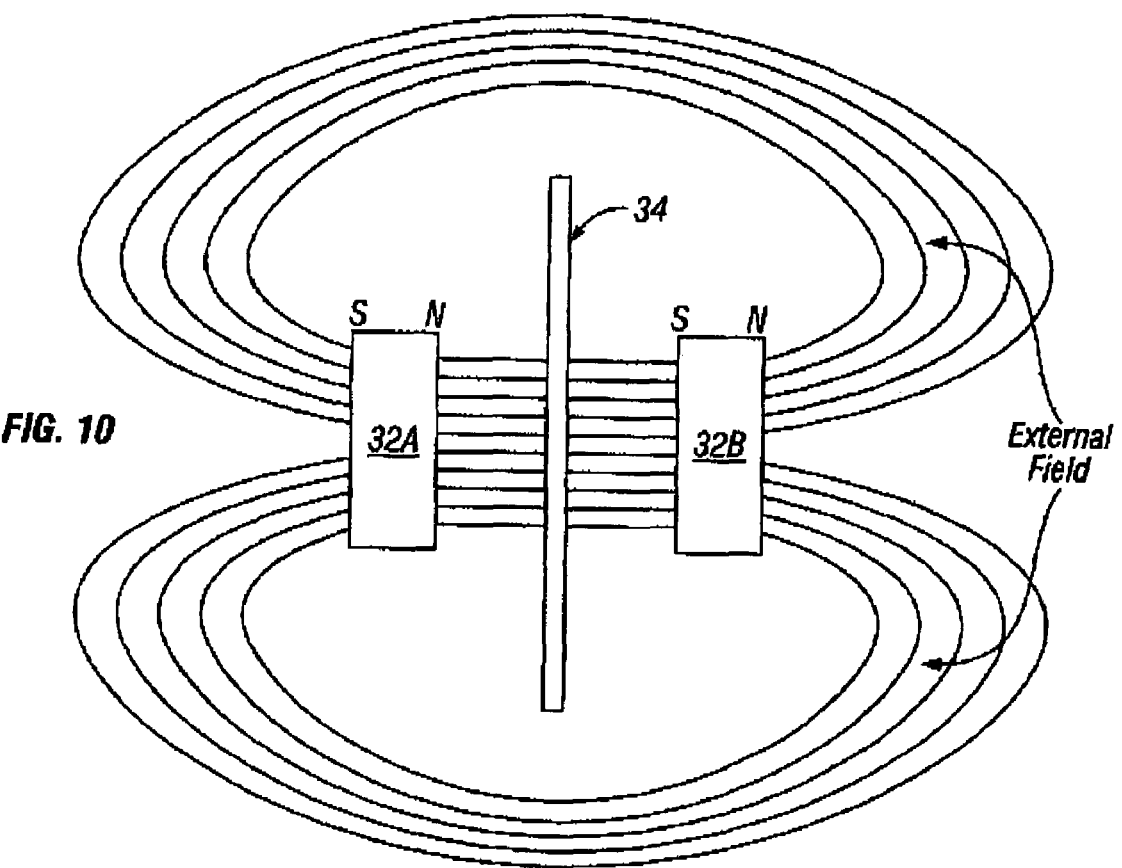

An alternative wand configuration, shown in FIG. 10, utilizes two permanent magnets 32A, 32B, as the magnetic field between them is less divergent than with a single permanent magnet. With the use of two permanent magnets 32A, 32B and less resultant divergence, there is less need for criticality about positioning the permanent magnet with respect to the sensor 34.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

We claim:

1. An apparatus for excluding ferromagnetic and magnetic objects from proximity to an MRI instrument, comprising:
    an array of sensors adapted to sense a magnetic field of an object;
    a processor adapted to interpret signals from said sensor array sensing said magnetic field to detect said object; and
    a scanner chassis on which said sensor array is mounted, said scanner chassis being adapted to position the entirety of said sensor array in proximity to all portions of a human subject, said scanner chassis being adapted to orient said sensor array to distinguish between a background magnetic field and said magnetic field of said object.

2. The apparatus recited in claim 1, wherein:
    said object is a "soft" ferromagnetic object; and
    said magnetic field comprises an induced magnetic field caused by magnetization of said ferromagnetic object by an external magnetic field.

3. The apparatus recited in claim 1, wherein said object comprises a permanently magnetic object.

4. The apparatus recited in claim 1, wherein said processor is further adapted to interpret signals from said sensor array sensing said magnetic field to characterize said object.

5. The apparatus recited in claim 1, wherein said processor is further adapted to interpret signals from said sensor array sensing said magnetic field to locate said object.

6. The apparatus recited in claim 1, wherein said scanner chassis comprises a portal structure, said portal structure having at least first and second vertical members, one of said vertical members being arranged on each side of a passageway adapted for passage of a recumbent human subject.

7. The apparatus recited in claim 6, wherein:
    said sensor array comprises at least first and second sensor sub-arrays;
    said first sensor sub-array is arranged horizontally on said first vertical member on a first side of said passageway;
    said second sensor sub-array is arranged horizontally on said second vertical member on a second side of said passageway; and
    said first and second sensor sub-arrays are positioned at a height matching a selected height at which said recumbent human subject will pass through said portal structure.

8. The apparatus recited in claim 6, wherein:
    said portal structure further comprises a horizontal member spanning said passageway between said first and second vertical members;
    said sensor array comprises at least one sensor sub-array arranged horizontally on said horizontal member; and
    said sensor sub-array is arranged above said passageway, at a height above, but in close proximity to, a selected height at which said recumbent human subject will pass through said portal structure.

9. The apparatus recited in claim 8, wherein:
    said horizontal member has a scanning position spanning said passageway at an intermediate height relative to said first and second vertical members, said scanning position limiting the clear height of said passageway between said first and second vertical members to said intermediate height; and
    said horizontal member has a non-scanning position, said non-scanning position not spanning said passageway at said intermediate height, said non-scanning position increasing said clear height of said passageway to allow passage of an upright human subject through said portal structure.

10. The apparatus recited in claim 9, wherein:
    said sensor array comprises at least three said sensor sub-arrays;
    a first said sensor sub-array is arranged horizontally on said horizontal member;
    a second said sensor sub-array is arranged vertically on said first vertical member;
    a third said sensor sub-array is arranged vertically on said second vertical member; and
    when said horizontal member is in said non-scanning position, said second and third sensor sub-arrays are adapted to scan said upright human subject passing through said portal structure.

11. The apparatus recited in claim 1, wherein said scanner chassis comprises a hand-held frame.

12. The apparatus recited in claim 11, wherein:
said object is a "soft" ferromagnetic object; and
said magnetic field comprises an induced magnetic field caused by magnetization of said ferromagnetic object by an external magnetic field.

13. The apparatus recited in claim 12, further comprising a source of said external magnetic field mounted on said hand-held frame.

14. The apparatus recited in claim 13, wherein said source of said external magnetic field comprises a permanent magnet.

15. The apparatus recited in claim 13, wherein said source of said external magnetic field comprises an electromagnetic coil.

16. The apparatus recited in claim 15, wherein said electromagnetic coil is driven by a DC source.

17. The apparatus recited in claim 15, wherein said electromagnetic coil is driven by an AC source.

18. The apparatus recited in claim 17, wherein said AC source operates at a frequency less than about 1000 Hz.

19. The apparatus recited in claim 13, wherein said sensor array comprises at least two sensors, said at least two sensors being arranged symmetrically relative to said magnetic field source, said at least two sensors being connected to cancel out their respective signals resulting from exposure to the flux of said magnetic field source.

20. The apparatus recited in claim 19, wherein said at least two sensors comprise induction coils.

21. The apparatus recited in claim 20, wherein each said induction coil is wound on a magnetically impermeable core.

22. The apparatus recited in claim 20, wherein each said induction coil is wound on a magnetically permeable core.

23. The apparatus recited in claim 19, wherein said at least two sensors comprise magnetometers.

24. An apparatus for excluding ferromagnetic objects from proximity to an MRI instrument, comprising:
a portal structure, said portal structure having at least first and second vertical members, one of said vertical members being arranged on each side of a passageway adapted for passage of a recumbent human subject, said portal structure having a horizontal member spanning said passageway between said first and second vertical members;
an array of sensors arranged horizontally on said horizontal member, said sensor array being adapted to detect an induced magnetic field caused by magnetization of a ferromagnetic object by an external magnetic field, said sensor array being adapted to distinguish between a background magnetic field and said induced magnetic field of said ferromagnetic object, a sensor sub-array being arranged above said passageway, at a height above, but in close proximity to, a selected height at which said recumbent human subject will pass through said portal structure; and
a processor adapted to interpret signals from said sensor array to detect said ferromagnetic object according to said induced magnetic field.

25. The apparatus recited in claim 24, wherein:
said horizontal member has a scanning position spanning said passageway at an intermediate height relative to said first and second vertical members, said scanning position limiting the clear height of said passageway between said first and second vertical members to said intermediate height; and
said horizontal member has a non-scanning position, said non-scanning position not spanning said passageway at said intermediate height, said non-scanning position increasing said clear height of said passageway to allow passage of an upright human subject through said portal structure.

26. The apparatus recited in claim 25, further comprising first and second vertical sensor arrays, wherein:
said first vertical sensor array is arranged vertically on said first vertical member;
said second vertical sensor array is arranged vertically on said second vertical member; and
when said horizontal member is in said non-scanning position, said first and second vertical sensor arrays are adapted to scan said upright human subject passing through said portal structure.

27. The apparatus recited in claim 19, further comprising:
a processor adapted to interpret signals from said sensor array to detect said ferromagnetic object according to said induced magnetic field.

28. The apparatus recited in claim 27, wherein said source of said magnetic field comprises a permanent magnet.

29. The apparatus recited in claim 27, wherein said source of said magnetic field comprises an electromagnetic coil.

30. The apparatus recited in claim 29, wherein said electromagnetic coil is driven by a DC source.

31. The apparatus recited in claim 29, wherein said electromagnetic coil is driven by an AC source.

32. The apparatus recited in claim 31, wherein said AC source operates at a frequency less than 1000 Hz.

33. The apparatus recited in claim 27, wherein said at least two sensors comprise induction coils.

34. The apparatus recited in claim 33, wherein each said induction coil is wound on a magnetically impermeable core.

35. The apparatus recited in claim 33, wherein each said induction coil is wound on a magnetically permeable core.

36. The apparatus recited in claim 27, wherein said at least two sensors comprise magnetometers.

37. The apparatus recited in claim 6, wherein:
said object is a "soft" ferromagnetic object; and
said magnetic field comprises an induced magnetic field caused by magnetization of said ferromagnetic object by an external magnetic field.

38. The apparatus recited in claim 37, further comprising at least one source of said external magnetic field mounted on said portal structure.

39. The apparatus recited in claim 38, wherein said at least one source of said external magnetic field comprises at least one permanent magnet.

40. The apparatus recited in claim 38, wherein said at least one source of said external magnetic field comprises at least one electromagnetic coil.

41. The apparatus recited in claim 40, wherein said at least one electromagnetic coil is driven by at least one DC source.

42. The apparatus recited in claim 40, wherein said at least one electromagnetic coil is driven by at least one AC source.

43. The apparatus recited in claim 42, wherein said at least one AC source operates at a frequency less than about 1000 Hz.

* * * * *